US006839580B2

(12) United States Patent
Zonios et al.

(10) Patent No.: US 6,839,580 B2
(45) Date of Patent: Jan. 4, 2005

(54) ADAPTIVE CALIBRATION FOR PULSE OXIMETRY

(75) Inventors: George Zonios, Ioannina (GR); Vijay K. Iyer, Export, PA (US); Uday S. Shankar, Alpharetta, GA (US)

(73) Assignee: RIC Investments, Inc., Wilmington, DE (US)

( * ) Notice: Subject to any disclaimer, the term of this patent is extended or adjusted under 35 U.S.C. 154(b) by 0 days.

(21) Appl. No.: 10/309,878

(22) Filed: Dec. 4, 2002

(65) Prior Publication Data

US 2003/0114738 A1 Jun. 19, 2003

Related U.S. Application Data

(60) Provisional application No. 60/337,515, filed on Dec. 6, 2001.

(51) Int. Cl.[7] .................................................. A61B 5/00

(52) U.S. Cl. ..................... 600/323; 600/330; 600/331

(58) Field of Search ............................ 600/322–323, 600/330–331, 309–310; 356/39–42; 357/39–42

(56) References Cited

U.S. PATENT DOCUMENTS

| | | | |
|---|---|---|---|
| 5,291,884 A | 3/1994 | Heinemann et al. | |
| 5,361,757 A | 11/1994 | Smith et al. | |
| 5,377,674 A | 1/1995 | Kuestner | |
| 5,551,424 A | 9/1996 | Morrison et al. | |
| 5,662,103 A | 9/1997 | Smith et al. | |
| 5,833,602 A | 11/1998 | Osemwota | |
| 5,911,689 A | 6/1999 | Smith et al. | |
| 6,151,107 A | * 11/2000 | Schollermann et al. | ....... 356/41 |
| 6,226,540 B1 | 5/2001 | Bernreuter | |
| 6,285,896 B1 | 9/2001 | Tobler et al. | |
| 6,298,253 B1 | 10/2001 | Buschmann | |
| 6,421,549 B1 | 7/2002 | Jacques | |

FOREIGN PATENT DOCUMENTS

WO WO 01/03577 A1 1/2001

OTHER PUBLICATIONS

Mannheimer et al., "Physio-Opitical Considerations in the Design of Fetal Pulse Oximetry Sensor," European Journal of Obstetrics & Gynecology and Reproductive Biology, 72 Suppl. 1, 1997.

Kock et al., Pulse Oximetry: Theoretical and Experimental Models, Med. & Bio. Eng. & Comput., vol. 31, pp. 291–300, 1993.

Marble, et al., "Diffusion–Based Model of Pulse Oximetry: In Vitro and In Vivo Comparisons," Applied Optics, vol. 33, No. 7, pp. 1279–1284, 1994.

Hamlin, "Guide to Pulse Oximetry Monitoring and Troubleshooting," Journal of Clinical Engineering, vol. 20, No. 6, pp. 476–483, 1995.

Fine et al., "Multiple Scattering Effect in Transmission Pulse Oximetry," Med. & Bio. Eng. & Comput., vol. 33, pp. 709–712, 1995.

Takatani et al., "Optical Oximetry Sensors for Whole Blood and Tissue," IEEE Engineering in Medicine and Biology, pp. 347–357, 1994.

(List continued on next page.)

Primary Examiner—Mary Beth Jones
Assistant Examiner—Matthew Kremer
(74) Attorney, Agent, or Firm—Michael W. Haas

(57) ABSTRACT

A method for calibrating a pulse oximeter device and an apparatus incorporating the method and a system for utilizing the method. The method is based on modeling light propagation in tissue at two wavelengths, typically, one in the red and one in the infrared range of the spectrum. A formula is derived relating the arterial oxygen saturation to a ratio R commonly measured by standard pulse oximeters. A specific parameter is identified and utilized in the calibration of the oximeter. This parameter is formulated in terms of the DC signals measured by the pulse oximeter at the two wavelengths. An empirical method for estimating this parameter based on experimental data is also described.

26 Claims, 9 Drawing Sheets

OTHER PUBLICATIONS

Kock et al., "In Vitro Investigation of the Factors Affecting Pulse Oximetry," Journal of Biomedical Engineering, vol. 13, pp. 61–66, 1991.

Schmitt, "Simple Photon Diffusion Analysis of the Effects of Multiple Scattering on Pulse Oximetry," IEEE Transactions on Biomedical Engineering, vol. 38, No. 12, pp. 1194–1203, 1991.

Nijland et al., "Assessment of Fetal Scalp Oxygen Saturation Determination in the Sheep by Transmission Pulse Oximetry," Am. J. Obstet. Gynecol., vol. 183, No. 3, pp. 1449–1553, 2000.

Masin et al., "Fetal Transmission Pulse Oximetry," Proceedings– 19th Int'l. Conf.—IEEE/EMBS, pp. 2326–2329, 1997.

* cited by examiner

ADAPTIVE CALIBRATION FOR PULSE OXIMETRY

BACKGROUND OF THE INVENTION

1. Field of the Invention

The present invention relates generally to optical measurement devices, and, more particularly, to pulse oximetry systems with a novel method of dynamically calibrating a pulse oximeter based upon empirical inputs and a related parameter that is a function of the DC component commonly measured in pulse oximetry.

2. Description of the Related Art

Oximetry is based on the principle that the color of blood is related to the oxygen saturation level of hemoglobin. For example, as blood deoxygenates, skin loses its pinkish appearance and takes on more of a bluish tint. This principle permits measurement of the degree of oxygen saturation of blood using what is commonly known as optical pulse oximetry technology.

Optical oximeters take advantage of the fact that oxygenated and deoxygenated hemoglobin absorb visible and near infrared light differently. Generally, blood perfused tissue is illuminated and light absorption by the tissue is determined by a suitable light sensor. The light absorption is then correlated with an estimated oxygen saturation level ($SaO_2$). In commonly used methods of pulse oximetry, the blood perfused tissue is illuminated by light selected to have at least two different wavelengths, preferably one in the red band and one in the infrared band.

A distinct absorption corresponds to each wavelength of light, such that a specific absorption corresponds to each hemoglobin oxygen saturation value in the range 0–100%. See e.g., *Physio-optical considerations in the design of fetal pulse oximetry sensors*, Mannheimer et al., European Journal of Obstetrics & Gynecology and Reproductive Biology, 72 Suppl. 1 (1997). Accurate oximeter performance requires a good overlap of light penetration in tissue at the chosen wavelengths so as to minimize the effects of tissue heterogenicity.

Pulse oximeter oxygen saturation level readings are denoted by $SpO_2$, whereas oxygen saturation in arterial blood samples based on direct in vitro measurement are denoted $SaO_2$. The pulse oximetry oxygen saturation level ($SpO_2$) is determined by positioning the blood-perfused tissue adjacent to a light source and a detector, passing a light of each of two wavelengths through the tissue, measuring the constant and pulsatile light intensities at each wavelength, and correlating them to an $SpO_2$ reading.

Values of light absorption measured in pulse oximetry generally include a constant (non-pulsatile) component and a variable (pulsatile) component. The constant component is commonly referred to as the "DC" component. The measured DC component is influenced by several factors, such as the light absorbency of the biological tissue, the presence of venous blood, capillary blood, and non-pulsatile arterial blood, the scattering properties of tissue, the intensity of the light source, and the sensitivity of the detector.

The variable component results from the pulsatile flow of arterial blood through the tissue being probed. This pulsatile flow, corresponding to the systole phase of the cardiac cycle, acts such that light absorption varies proportionately to the flow of blood. This variable absorption of light through tissue (the pulsatile component) is commonly referred to as the "AC" component. Because pulsing is a function of the fluctuating volume of arterial blood, the AC light intensity level fairly represents the light absorption of the oxygenated and deoxygenated hemoglobin of arterial blood.

To determine a ratio (R) of pulsatile light intensities to non-pulsatile light intensities, the constant DC component of the light intensity must be factored out. The amplitudes of both the AC and DC components are dependent on the incident light intensity. Dividing the AC level by the DC level gives a "corrected" AC level that is no longer a function of the incident light intensity. Thus, ratio $R=(AC1/DC1)/(AC2/DC2)$ is an indicator of arterial $SaO_2$. Conventionally, an empirically derived calibration curve for the relationship between the above ratio R and $SaO_2$ provides the pulse oximetry oxygen saturation level $SpO_2$.

In oximetry, the measured transmission of light traveling through blood-perfused tissue, and the pulse oximetry oxygen saturation level ($SpO_2$), are therefore based upon two things: one, the natural difference in light absorption in oxygenated hemoglobin and deoxygenated hemoglobin; and two, the detected change in light absorption resulting from the fluctuating volume of arterial blood passing through the tissue between the light source and the sensor, i.e., the pulsatile component. The amplitude of the pulsatile component is a small fraction of the total signal amplitude, so small changes in the pulsatile component may be "lost" in the background of the total signal amplitude.

By relying on the pulsatile component in this manner, current pulse oximeters and methodologies cannot effectively account for light scattering and absorption of light in the biological tissues that are being probed. Thus, current techniques use empirical data and factor in an average component for scattering and absorption. See e.g., *Pulse Oximetry: Theoretical and Experimental Models*. De Kock, et al., Medical and Biological Engineering & Computing, Vol. 31, (1993). This approach results in oximeters that rely upon fixed calibration curves to predict $SpO_2$ from measured electronic signals.

The current practice in pulse oximetry of subsuming the scattering and absorption of light that occurs in tissue by resorting to empirical calibration techniques is problematic. While it may be acceptable at oxygen saturation levels within normal ranges for adults, i.e., 70% to 100% $SaO_2$, it becomes less acceptable when oxygen saturation is in the lower range, for example, of 15% to 65% $SaO_2$. This lower range represents severe hypoxia in post-natal subjects, and is also commonly encountered in fetal oximetry. Both of these circumstances require accurate and reliable oxygen saturation estimates.

In oximeters with larger probes, e.g., probes having a pathlength between the emitter and detector that would encompass a finger, foot or earlobe, the conventional approach to calibration is acceptable because scatter and absorption are less of an issue. As the probe size decreases, however, and the pathlength becomes shorter, e.g., fetal oximeter probes, the error due to background scattering and absorption has a relatively greater impact on oximeter accuracy.

Precise estimation of $SpO_2$ with probes having a pathlength less than 5 mm is difficult due to the scattering and absorption of light in tissue. The challenge, therefore, is to account for scattering and absorption through their relationship to the measured DC and AC signals.

Approaches have been described in the literature wherein the scattering and absorption characteristics of the tissue being probed are theoretically modeled. See e.g., *Diffusion-based model of pulse oximetry: in vitro and in vivo*

*comparisons*, Marble et al., Applied Optics, Vol.33, No. 7 (1994); *Pulse Oximetry: Theoretical and Experimental Models*, Kock et al., Med. & Biol. Eng. & Comput., Vol. 31 (1993). One problem with the theoretical approach is that the total number of variables used in the various models make it difficult to accurately model these characteristics. This results in further approximations, and in an inevitable "guessing" of some of the parameters. For example, in order to calculate absorption from the DC signal, one has to guess scattering. Similarly, where one wants to calculate scattering from the DC signal, absorption has to be approximated.

Furthermore, inter-patient and intra-patient variation between the biological tissues that are probed, present a significant challenge to the purely theoretical approach. This variation precludes the modeling of scattering and absorption in a dynamic fashion. Neither the currently employed empirical approach, nor the theoretical models currently described, are as accurate or dynamic as the calibration techniques of the present invention.

The present invention differs from conventional techniques in that it does not use an arbitrary guess for scattering, but instead uses clinical data to evaluate an average scattering, and incorporates that value into a parameter identified as $k_{DC}$. In particular, the functional dependence of $k_{DC}$ on the measured signals AC and DC depends on the average scattering which is derived from the clinical studies.

SUMMARY OF THE INVENTION

In pulse oximetry, the intensity of light, T, transmitted through tissue is measured. The arterial oxygen saturation, $SaO_2$, is calculated from the changes introduced in T due to the time-varying volume, i.e., pulsing, of arterial blood and the different absorption properties of oxygenated and deoxygenated hemoglobin. Changes in arterial blood volume introduce corresponding changes to hemoglobin absorption, and hence, changes to the total absorption coefficient of light in tissue, $\mu_a$. In turn, these changes affect the light transmission measured signal T.

Determining oxygen saturation by pulse oximetry generally involves two steps. First, changes in the hemoglobin absorption of tissue due to the pulsatile flow of blood must be evaluated. The changes in hemoglobin absorption are dependent upon $SaO_2$. Second, the changes in the measured signal, T, must be related to the absorption changes such that: $T \rightarrow \mu_a \rightarrow SaO_2$.

In pulse oximetry, relating the changes in the measured signal T to the change in absorption $\mu_a$ poses problems. In essence, the challenge is in the nature of a radiative transport problem, namely, how to account for the absorption and scattering of light in biological tissue.

Accordingly, the present invention is an improved hybrid calibration methodology preferably based on a combination of theoretical and empirical inputs that account for the scattering and absorption of light in tissue. The calibration methods can be utilized in a dynamic manner so as to adaptively calibrate the oximeter based on changing inputs, thereby improving the accuracy and precision of the oxygen saturation predictions. The methodology is applicable over a wide range of oxygen saturation levels and a variety of probe configurations and sizes, but is particularly applicable to circumstances where lower oxygen saturation levels are typically encountered, and/or with probes having a relatively short pathlength between the emitter and detector.

Additionally, a method and apparatus for conducting pulse oximetry are provided that account for the scattering and absorption of light in biological tissue.

It is an object of the present invention to provide an improved calibration methodology that need not rely on fixed calibration curves. In particular, the present invention provides a method of calibrating a pulse oximeter wherein the light propagation in tissue is preferably modeled for two distinct wavelengths such that the effects of the scattering and absorption of light in the tissue are incorporated into the resulting oxygen saturation prediction. According to one aspect of the invention, the scattering and absorption of light in tissue are preferably formulated into a determinable parameter based on commonly measured values.

In a presently preferred embodiment, experimental data is gathered and assimilated such that a new parameter, $k_{DC}$, is determined to be a function of the typical measured DC value. In this manner, parameter $k_{DC}$ is calculated utilizing subsequently detected DC signals, and, therefore, a reference is made to previously obtained experimental data to accurately predict $SpO_2$ based upon the detected DC signal.

Also provided is a method of performing optical oximetry wherein light is transmitted, detected and measured, and the resulting measurements are used to formulate a corresponding ratio R. The DC signals are measured and used to calculate $k_{DC}$ and then $k_{DC}$ and R are multiplied together and are used together and the resulting value is used to determine an $SpO_2$ value.

In another embodiment, a processing system is provided to control the emission of light, the detection of light, the calibration of the detected signals based on the methods described herein, and to calculate and predict $SaO_2$.

In a presently preferred embodiment, the calculating step incorporates the measured DC value. In other embodiments, the calculating step also incorporates the partial derivative $D_r$ in the calculation of $k_{DC}$ The calculating step incorporates changes in the scattering and absorption of light in tissue as a function of the measured signals, thereby allowing for an adaptive method of calibrating an oximeter.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

and
which is shown in Equation (20) and used in Equation (21).

DETAILED DESCRIPTION OF THE PRESENTLY PREFERRED EMBODIMENTS OF THE INVENTION

Figure 1:
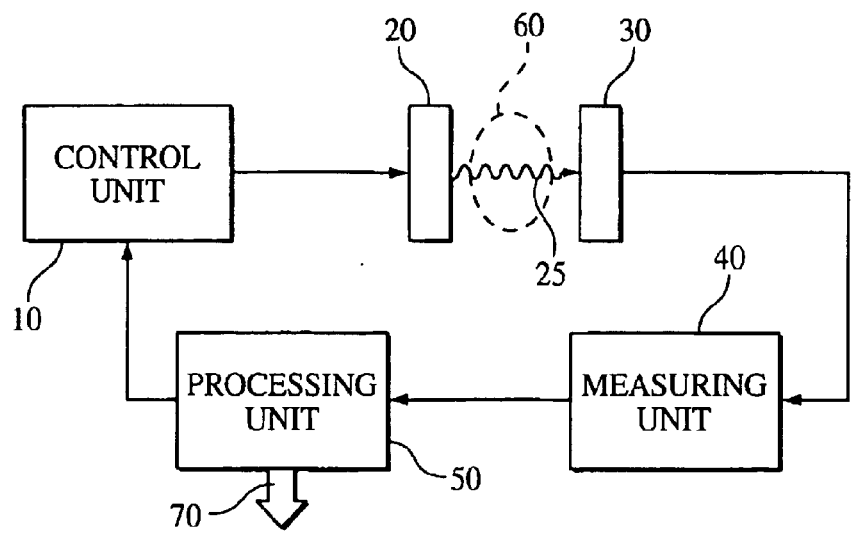
FIG. 1 is a diagram showing one arrangement of components suitable for use to practice oximetry technique and the method of calibrating an oximeter in accordance with the principles of the present invention.

The oximetry measurement devices, calibration systems and methodologies of the present invention are applicable to most, if not all, current oximetry devices and practices. For example, FIG. 1 depicts a block diagram showing the general arrangement of an oximetry system that includes a control unit 10, a light source 20, a light detector 30, a measuring unit 40, and a processing unit 50. Control unit 10 is coupled to light source 20 to activate the transmission of light. To practice the present invention, tissue 60 is positioned between (for transmission oximetry) or against (for reflectance oximetry) light source 20 and light detector 30. In this arrangement, light source 20 outputs light of one or more wavelengths, and preferably two or more wavelengths, wherein at least one wavelength is in the red range and one in the infrared (ir) range.

Processing unit 50 is coupled to control unit 10 to coordinate the transmitted light and detected light. Light source 20 produces light having the desired wavelength(s) which is then transmitted through the tissue 60 to light detector 30 along optical measurement path 25. Light detector 30 is coupled to measuring unit 40, which measures the light intensity incident on light detector 30. Measuring unit 40 is coupled to processor unit 50, which receives and processes the light intensity measurement to produce measurement 70. Measurement 70 is typically the result of processing light intensity measurement T into the output $SpO_2$.

Figure 2A:
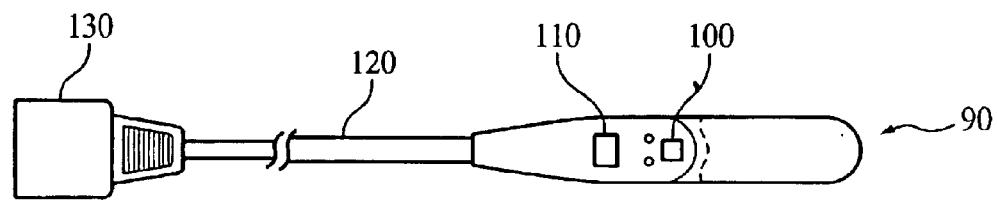
FIG. 2A is an example of a reflectance-type probe.

In accordance with the present invention, the process of transmitting and detecting light through tissue can be undertaken in a variety of ways. For example, FIG. 2A shows a reflectance probe 90 wherein a light source 100 is placed near the tissue to be probed, and light is emitted into the tissue. Light is reflected back out of the tissue and is detected by detector 110, 30, which sends a signal via cable 120 and connector 130 to a pulse oximeter processor and monitor (not shown) and processed.

Figure 2B:
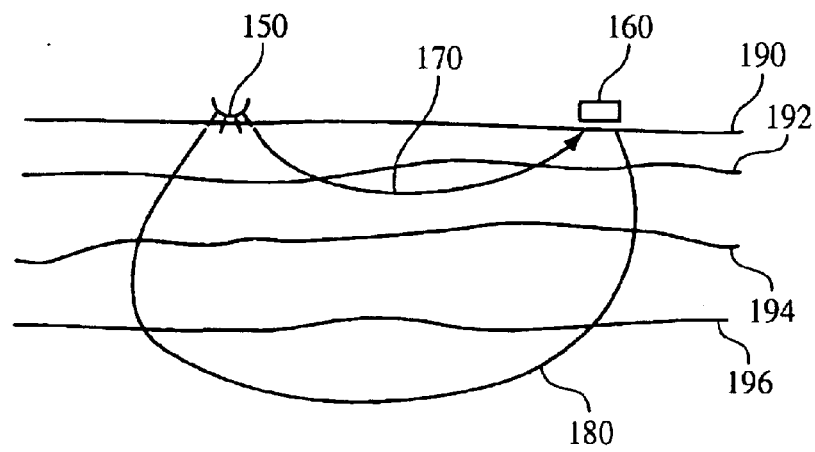
FIG. 2B is a depiction of a non-invasive oximetry technique.

As schematically shown in FIG. 2B, it is well known to use multiple wavelengths of light in reflectance (as well as transmission) oximetry. Typically a red 170 and an ir 180 wavelength are chosen whereby the differing wavelengths of light pass through discrete layers of the tissue, e.g., skin 190, fat 192, muscle 194 and bone 196, being probed.

Figure 3A:
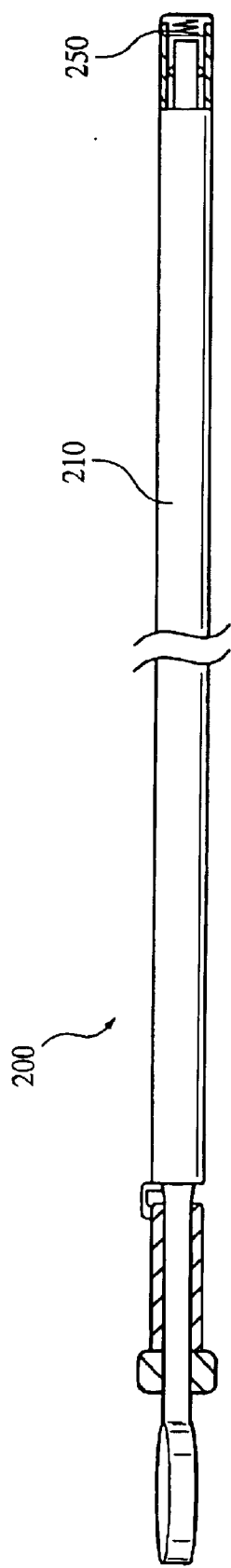
FIG. 3A is an example of a transmission-type probe commonly used in conducting fetal oximetry.
Figure 3B:
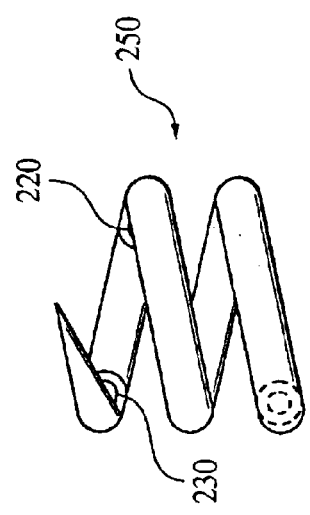
FIG. 3B is an enlargement of the sensor of FIG. 3A showing a spiral needle and depicting the location of a light source and detector for an invasive oximetry probe.

FIG. 3A shows an example of an invasive probe 200 that is commonly used in conducting fetal oximetry. A light source and detector on a sensor 250 is imbedded subcutaneously into the fetal tissue. FIG. 3A shows the sensor housed in a sheath 210 prior to being placed in a patient. FIG. 3B shows an enlargement of probe/sensor 250. In this spiral needle probe 250, a light emitter 220 and a light detector 230 are in very close proximity, such as less than one centimeter apart. Other types of transmission-probe arrangements that are non-invasive and/or allow the transmission of light through an ear lobe or finger, typically will have a greater distance, and hence a longer pathlength, between the light source and light detector.

The specific aspects of the present invention are described without reference to any one particular type of probe, because the calibration techniques of the present invention are applicable to all types of oximetry devices. Thus, the calibration techniques of the present invention are suitable for use with reflectance-type probes, like those shown in FIG. 2A, and transmissive-type probes, like those shown in FIGS. 3A and 3B, as well as any other invasive or non-invasive probes. In addition to these probe types, the systems and methodologies of the invention are applicable to virtually any type of oximetry probe configuration.

To practice the invention with any type of measuring device or system, e.g., transmission, reflectance, invasive, non-invasive, what is needed is to determine the relationship between the probe geometry and measured signal T, and then to develop appropriate calibration curves or equations through clinical trials. This process is shown generally in FIG. 4A and is discussed in greater detail with reference to FIG. 4B.

I. Basic Oximetry Calibration Equations

Pulse oximetry generally utilizes two wavelengths of light, one in the red wavelength (red) range (typically 630–760 nm) and one in the infrared wavelength (ir) range (typically 880–960 nm). The absorption coefficients of oxygenated hemoglobin and deoxygenated hemoglobin at red can be represented as $\mu_{OX}$ (red) and $\mu_{DX}$ (red), respectively. Similarly, the corresponding absorption coefficients at infrared (ir) can be represented as $\mu_{OX}$ (ir) and $\mu_{DX}$ (ir).

By designating the total concentrations of oxygenated and deoxygenated hemoglobin as $c_{OX}$ and $c_{DX}$ respectively, the total hemoglobin absorption of light for each of the red and ir wavelengths, $\mu_a$, can be given by Equations (1) and (2) such that:

$$\mu_a(\text{red}) = c_{OX}\mu_{OX}(\text{red}) + c_{DX}\mu_{DX}(\text{red}) \quad \text{(Equation 1)}$$

$$\mu_a(ir) = c_{OX}\mu_{OX}(ir) + c_{DX}\mu_{DX}(ir) \quad \text{(Equation 2)}$$

Equations (1) and (2) can then be solved to obtain the total oxygenated ($c_{OX}$) and deoxygenated ($c_{DX}$) hemoglobin concentrations such that:

$$c_{OX} = \frac{\mu_a(\text{red})\mu_{DX}(ir) - \mu_a(ir)\mu_{DX}(\text{red})}{\mu_{OX}(\text{red})\mu_{DX}(ir) - \mu_{OX}(ir)\mu_{DX}(\text{red})} \quad \text{(Equation 3)}$$

$$c_{DX} = \frac{\mu_a(ir)\mu_{OX}(\text{red}) - \mu_a(\text{red})\mu_{OX}(ir)}{\mu_{OX}(\text{red})\mu_{DX}(ir) - \mu_{OX}(ir)\mu_{DX}(\text{red})} \quad \text{(Equation 4)}$$

As noted above, arterial pulses (corresponding to the systolic portion of the cardiac cycle) cause an increase in the volume of arterial blood in the tissue being probed, i.e., a pulsatile change. This increase in arterial blood introduces a corresponding change in the oxygenated and deoxygenated hemoglobin concentrations. These changes can be denoted $c'_{OX}$ and $c'_{DX}$ respectively. As a consequence of the pulsatile change in arterial blood volume, the total hemoglobin absorption of light, $\mu_a$, also changes for each of the red and ir wavelengths, and can be given by Equations (5) and (6) such that:

$$\mu'_a(\text{red}) = c'_{OX}\mu_{OX}(\text{red}) + c'_{DX}\mu_{DX}(\text{red}) \quad \text{(Equation 5)}$$

$$\mu'_a(ir) = c'_{OX}\mu_{OX}(ir) + c'_{DX}\mu_{DX}(ir) \quad \text{(Equation 6)}$$

Equations (5) and (6) can then be solved to obtain the total change in the oxygenated and deoxygenated hemoglobin concentrations attributable to arterial pulsing ($c'_{OX}$ and $c'_{DX}$) such that:

$$c'_{OX} = \frac{\mu'_a(\text{red})\mu_{DX}(ir) - \mu'_a(ir)\mu_{DX}(\text{red})}{\mu_{OX}(\text{red})\mu_{DX}(ir) - \mu_{OX}(ir)\mu_{DX}(\text{red})} \quad \text{(Equation 7)}$$

$$c'_{DX} = \frac{\mu'_a(ir)\mu_{OX}(\text{red}) - \mu'_a(\text{red})\mu_{OX}(ir)}{\mu_{OX}(\text{red})\mu_{DX}(ir) - \mu_{OX}(ir)\mu_{DX}(\text{red})}. \quad \text{(Equation 8)}$$

The saturation of arterial hemoglobin, $SpO_2$, is then given by Equation (9) as follows:

$$SpO_2 = \frac{c'_{OX} - c_{OX}}{(c'_{OX} - c_{OX}) + (c'_{DX} - c_{DX})} = \frac{1}{1 - \frac{x\mu_{OX}(ir) - \mu_{OX}(\text{red})}{x\mu_{DX}(ir) - \mu_{DX}(\text{red})}} \quad \text{(Equation 9)}$$

In Equation (9), parameter x is defined by Equation (10) such that:

$$x = \frac{\mu'_a(\text{red}) - \mu_a(\text{red})}{\mu'_a(ir) - \mu_a(ir)} = \frac{\Delta\mu_a(\text{red})}{\Delta\mu_a(ir)}. \quad \text{(Equation 10)}$$

According to Equation (9), the arterial hemoglobin saturation is a function of x, which represents the fractional change in the absorption coefficient $\mu_a$, at the two wavelengths of interest, one red and one ir.

II. Introduction of $k_{DC}$

Accurate oximetry depends upon being able to relate the changes in absorption to the measured signal T. A small change in the absorption coefficient, $\Delta\mu_a$, introduces a corresponding change, $\Delta T$, to the measured signal T. In general, the AC signal is proportional to $\Delta T$, and the DC signal is proportional to T as shown by Equation (11) such that:

$$\Delta T = \frac{\partial T}{\partial \mu_a}\Delta\mu_a \Rightarrow \Delta\mu_a = \frac{(AC)}{\frac{\partial T}{\partial \mu_a}\Big|_{\mu_a=\mu_a(DC)}} \quad \text{(Equation 11)}$$

Note that Equation (11) requires knowledge of the dependence of the measured signal T on the absorption $\mu_a$. In general, T is a function of the scattering and absorption coefficients denoted $\mu'_s$ and $\mu_a$, respectively, such that: $T=T(\mu_a, \mu'_s)$.

The exact form of $T(\mu_a, \mu'_s)$ depends on the specific probe geometry employed for the delivery (transmission) and collection (detection) of the light. In general, T cannot be fully derived theoretically, because the equation it obeys (i.e., the radiative transfer equation, plus the appropriate boundary conditions) cannot be solved theoretically. The dependence of T on scattering and absorption can, however, be determined experimentally for a given probe geometry. One way that this can be done, for example, is by using a series of tissue phantoms with known scattering and absorption properties. Another way is to conduct clinical trials with experimental subjects. Once T is determined experimentally, (either with tissue phantoms or experimental subjects) the expression can be inverted and rewritten as shown by Equation (12) such that:

$$\mu_a = \mu_a(T, \mu'_s) \quad \text{(Equation 12)}$$

and the derivative in Equation (11) can thus be evaluated.

Equation (12) can then be used to calculate the fractional change in the absorption x in terms of the AC and DC signals for that particular probe, i.e., signals typically measured by oximeters, such that:

$$x = \frac{\Delta\mu_a(\text{red})}{\Delta\mu_a(ir)} = \frac{\frac{\partial T}{\partial \mu_a}\Big|_{\mu_a=\mu_a(ir)} AC(\text{red})}{\frac{\partial T}{\partial \mu_a}\Big|_{\mu_a=\mu_a(\text{red})} AC(ir)} \Rightarrow x = k_{DC}R \quad \text{(Equation 13)}$$

with $$k_{DC} = \frac{\frac{\partial T}{\partial \mu_a}\Big|_{\mu_a=\mu_a(ir)} DC(\text{red})}{\frac{\partial T}{\partial \mu_a}\Big|_{\mu_a=\mu_a(\text{red})} DC(ir)} \quad \text{(Equation 14)}$$

and $$R = \frac{(AC)/(DC)|_{red}}{(AC)/(DC)|_{ir}} \quad \text{(Equation 15)}$$

Thus, parameter $k_{DC}$ is a function of the DC signal only, and R is the AC/DC ratio as defined in pulse oximetry. As shown above, parameter $k_{DC}$ incorporates the effects of scattering and absorption. Accordingly, for a given value of $k_{DC}$, there is a corresponding calibration curve $SaO_2(R)$. Thus, the dependence of $SaO_2$ on R is fully defined and fixed, once $k_{DC}$ is fixed. (In that sense, a new $k_{DC}$ value corresponds to a new $SaO_2$ vs. R curve).

In traditional pulse oximetry, scattering is ignored and the Beer-Lambert exponential attenuation of light in tissue is assumed to hold such that $T=e^{-\mu_a L}$, where L is the tissue thickness. Under this assumption, $$\Delta\mu_a = -\frac{1}{L}\frac{\Delta T}{T} = \quad \text{(Equation 16)}$$

$$-\frac{1}{L}\frac{(AC)}{(DC)} \Rightarrow x = \frac{\Delta\mu_a(\text{red})}{\Delta\mu_a(ir)} = \frac{(AC)/(DC)|_{red}}{(AC)/(DC)|_{ir}} = R$$

Inserting the above result into Equation (13) confirms that the basic approximation of traditional pulse oximetry is expressed by $k_{DC}=1$, i.e., the effects of background absorption and scattering are ignored, when, however, it is known that $k_{DC}$ is not always equal to 1.

Determining $k_{DC}$ using the approach outlined in Equation (14) provides for a better accounting of the absorption and scattering of light in biological tissue compared to the traditional approach of ignoring the effects of background absorption and scattering. In this way, the introduction of the $k_{DC}$ parameter represents a significant improvement in the calibration of a pulse oximeter by employing both empirical and theoretical inputs into the prediction equation.

III. Use of $k_{DC}$ to Determine Oxygen Saturation

Figure 4A:
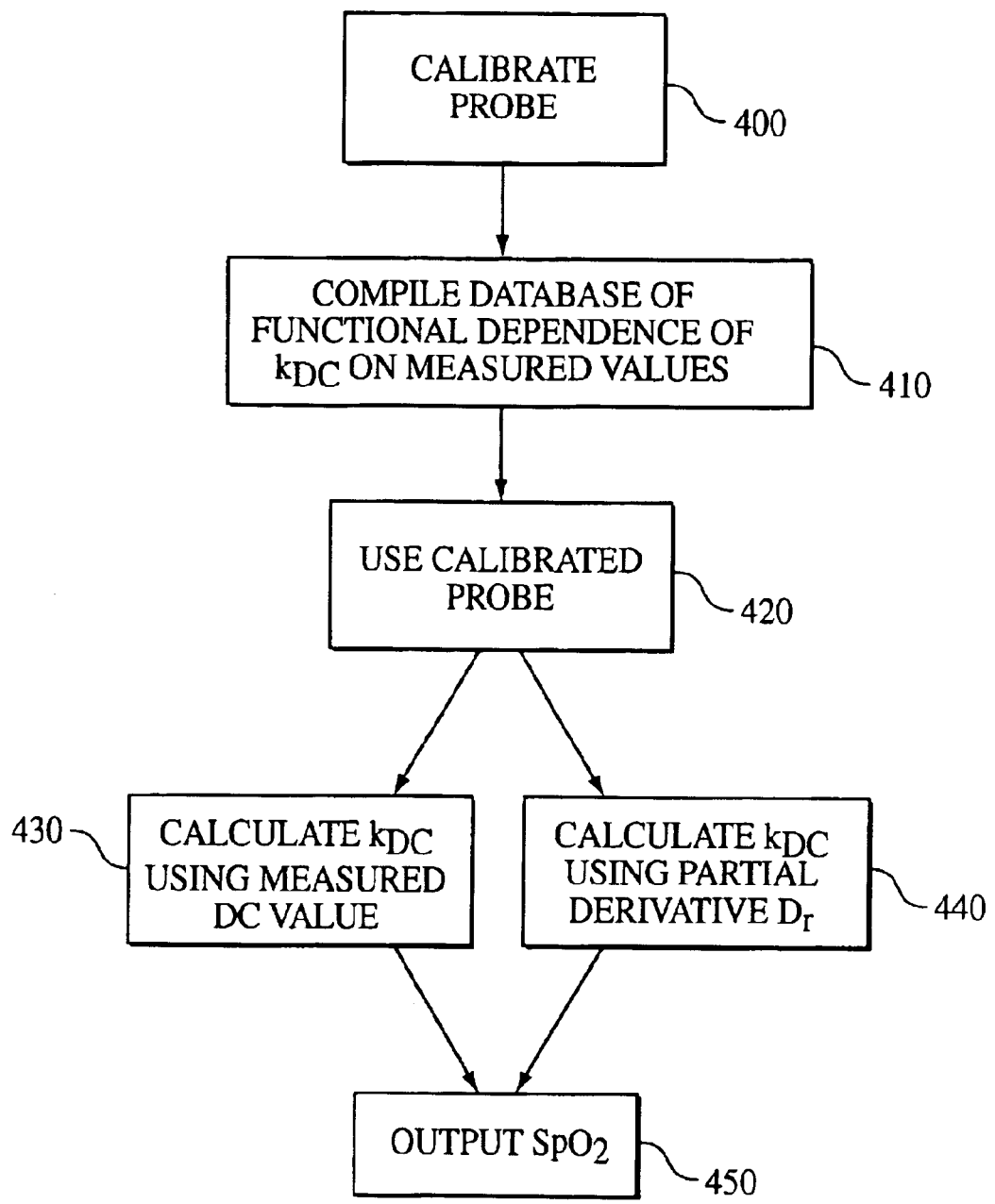
FIG. 4A is a generalized flow diagram of the process of the present invention.

The calibration techniques of the invention are applicable to all types of measuring devices. To practice the invention with any type of measuring device, what is required, in general terms is to determine the relationship between the probe geometry, the measured signals, and to develop the appropriate calibration curves for example, through clinical trials. FIG. 4A describes the general process of the present invention. For example, in step 400 the probe is calibrated using experimental subjects and by conducting clinical trials as described in detail below in "Confirmation of $k_{DC}$ Clinical Evaluation." Alternately, tissue phantoms with known light scattering and light absorption properties may be employed. The data obtained in step 400 is compiled into a database in step 410.

Once the probe has been calibrated in step 400 and the data compiled in step 410, the oximetry device is used on prospective subjects in step 420. By measuring the AC and DC signals (i.e. signals normally measured) during step 420, and comparing the measured signals to the database 410, a value for $k_{DC}$ can be determined.

One method of obtaining $k_{DC}$ is by determining its functional dependence on DC, as generally outlined in step 430. Another method of obtaining $k_{DC}$ is by determining its functional dependence on derivative $D_r$, as generally outlined in step 440. Once $k_{DC}$ is obtained by either pathway 430, 440 (or through other means), the value for $k_{DC}$ is used to arrive at an $SpO_2$ value that accounts for the scattering and absorption of light 450 and accurately reflects the subjects $SaO_2$ status.

Figure 4B:
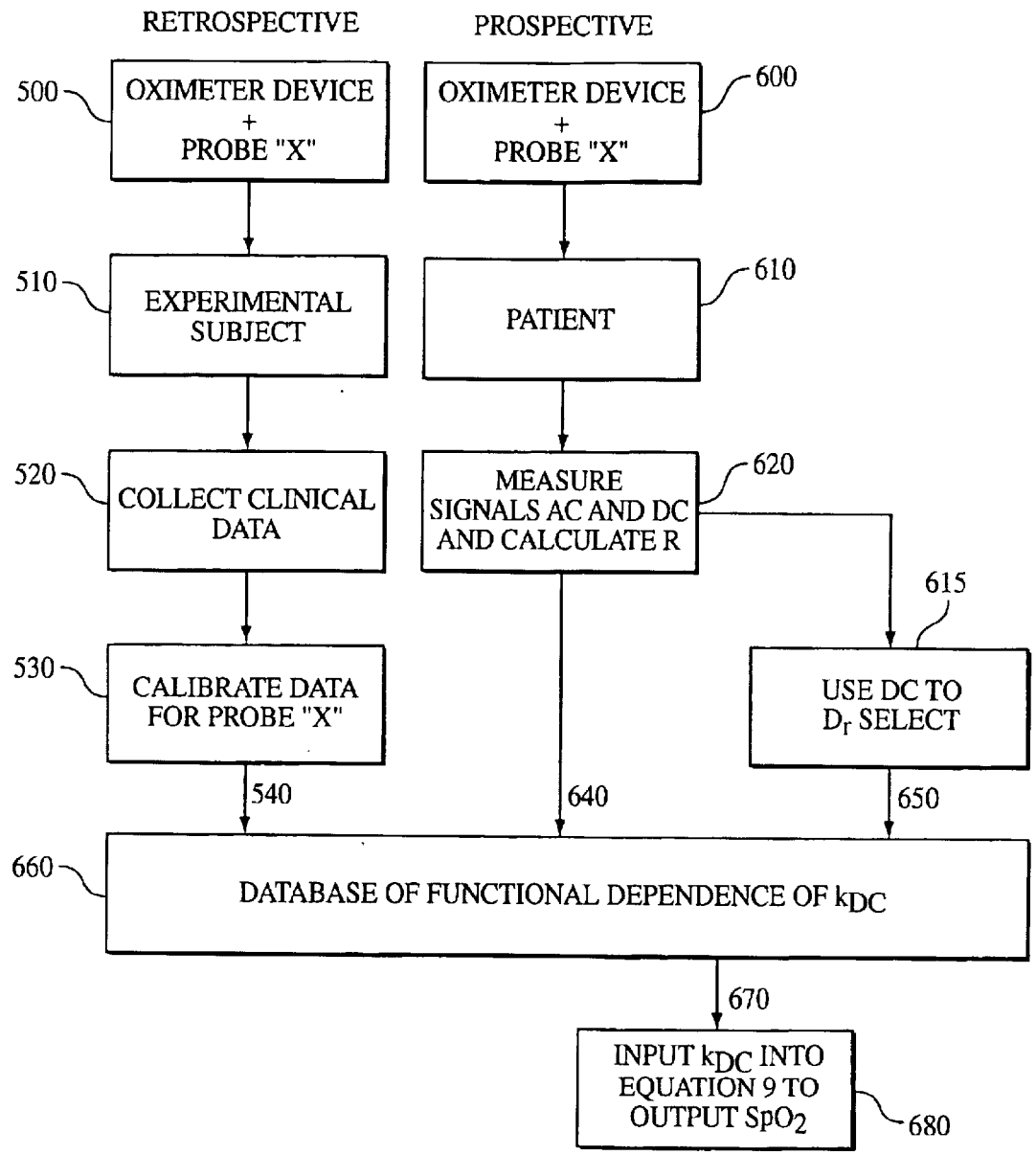
FIG. 4B is a detailed schematic flow diagram showing both Prospective and Retrospective sequences of (i) obtaining calibration data, and (ii) using the oximeter with the calibration data in accordance with the present invention.

Specifically, this process is undertaken, in an exemplary embodiment of the present invention, as described in FIG. 4B. For example, on the "Retrospective" side of the flow chart, the process begins by selecting 500 an oximeter device and a probe having a red and ir source of light and a fixed path length between the light source and detector. Through the use of an experimental subject 510, the relationship between the measured signals and the blood gas $SaO_2$ value are determined by subjecting the probe to one or more clinical trials and characterizing, and collecting the data 520.

Figure 8:
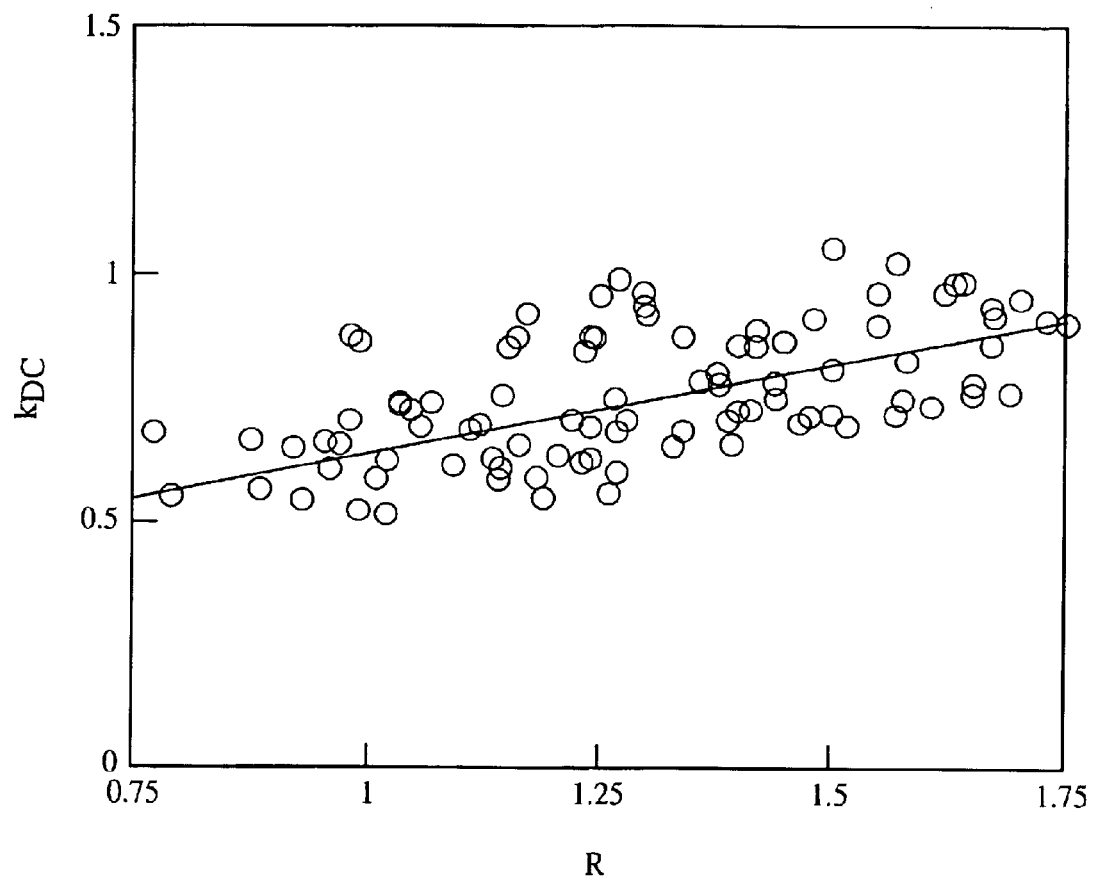
FIG. 8 shows the linear relationship between $k_{DC}$ and R for the clinical data and which can be represented by Equation (22)
Figure 9:
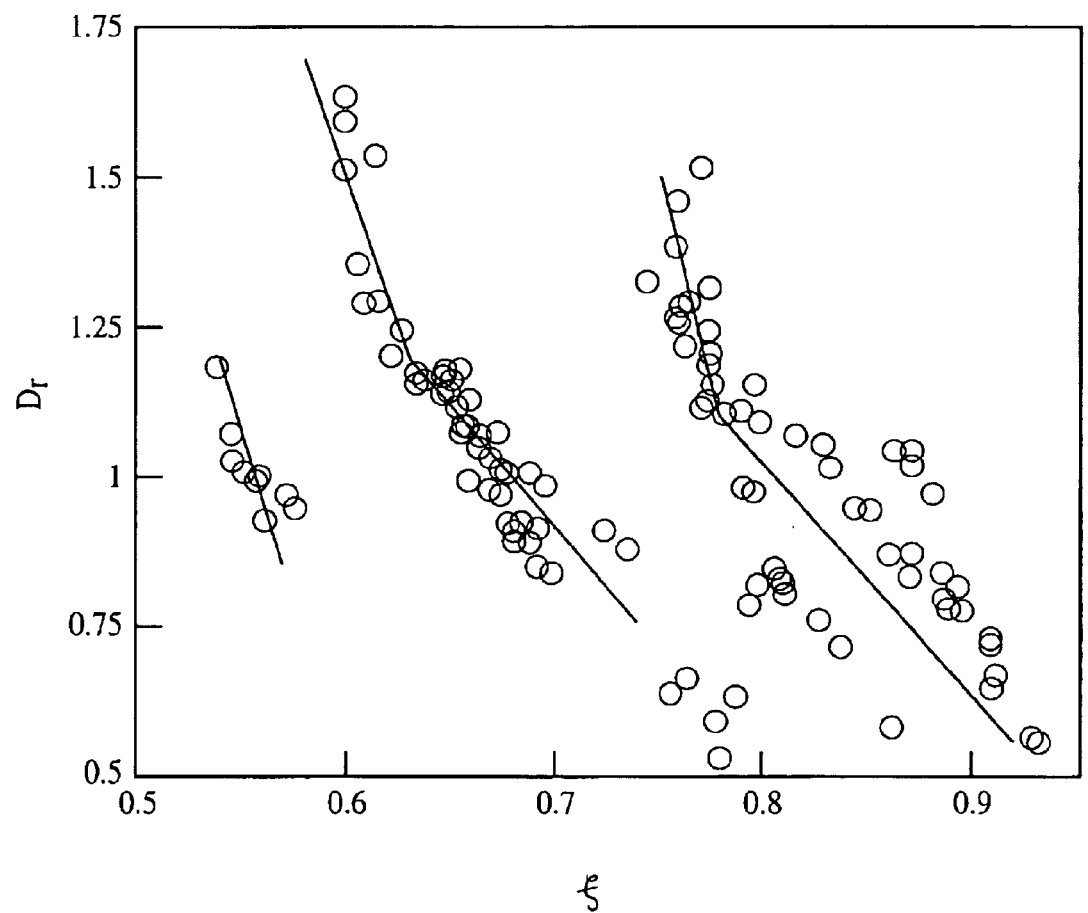
FIG. 9 shows the relationship between $D_r$ and Ratio $$\xi = \frac{DC(red)}{DC(ir)}$$

Once the data has been collected, the relationship is developed and the probe is calibrated 530 from the clinical data by estimating the functional dependence of parameter $k_{DC}$ on the measured DC ratio over a range of $SaO_2$ oxygen saturations. This calibration data is compiled 540 into database of functional dependence of $k_{DC}$ 660 on one or more measured variables, e.g., on R as depicted in FIG. 8, or as depicted in FIG. 9.

Once these retrospective steps have been undertaken, oximetry proceeds in typical fashion, for instance, as shown in FIG. 4B on the "Prospective" side of the flow chart. With reference to FIG. 4B, after connecting the pre-calibrated probe to an oximeter device 600, oximetry can proceed as described below.

First, the probe is located such that the patient's tissue of interest 610 is between (for transmission oximetry) or adjacent to (for reflectance oximetry) the light source and light detector. Next, light is transmitted through the patient's tissue 610 and the AC and DC values are measured 620 and the Ratio (R) of pulsatile light intensities to non-pulsatile light intensities are calculated using Equation (15).

At this point, ratio R is used to arrive at a value for $k_{DC}$ in a number of ways. One avenue is to go directly to the database of functional dependence of $k_{DC}$ 660 via step 640. FIG. 8 (discussed below) depicts an example of the functional dependence of $k_{DC}$ on R. In proceeding along this path 640, the Equation (22), as shown and discussed below, is used to obtain $k_{DC}$. After arriving at a value for $k_{DC}$ in this manner, the $k_{DC}$ value is inputted 670 into Equation (9) and an $SpO_2$ value is generated in step 680.

An alternate pathway to $k_{DC}$ from step 620 is through step 615. In step 615 the measured DC signals are used to select derivative variable $D_r$ via the Ratio $$\xi = \frac{DC(\text{red})}{DC(ir)}.$$

Variable $D_r$ is defined by Equation (18) which is discussed in detail and shown below. In this manner, a table of expressions can be formulated over a range of ratios. With reference to FIG. 9, a graphical example of the data obtained in step 615 is shown. Following the derivation of $D_r$ in step 615, $k_{DC}$ can be determined by 650 entry into the previously compiled database 660. The parameter $k_{DC}$ can then be obtained using Equation (21). Via step 670, $k_{DC}$ is input such that $SpO_2$ can be output with Equation (9) in step 680.

IV. Confirmation of $k_{DC}$ Via Clinical Evaluation

Figure 5A:
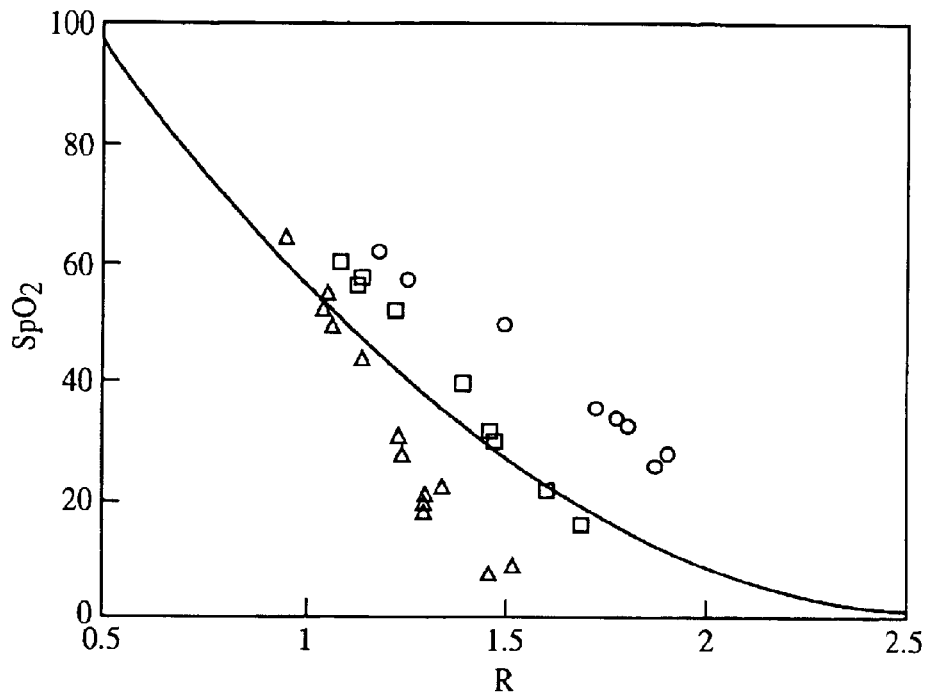
FIG. 5A shows the calibration curve $SpO_2$ vs. R obtained by employing a prior art method to obtain a fixed calibration curve for data from three clinical cases.
Figure 5B:
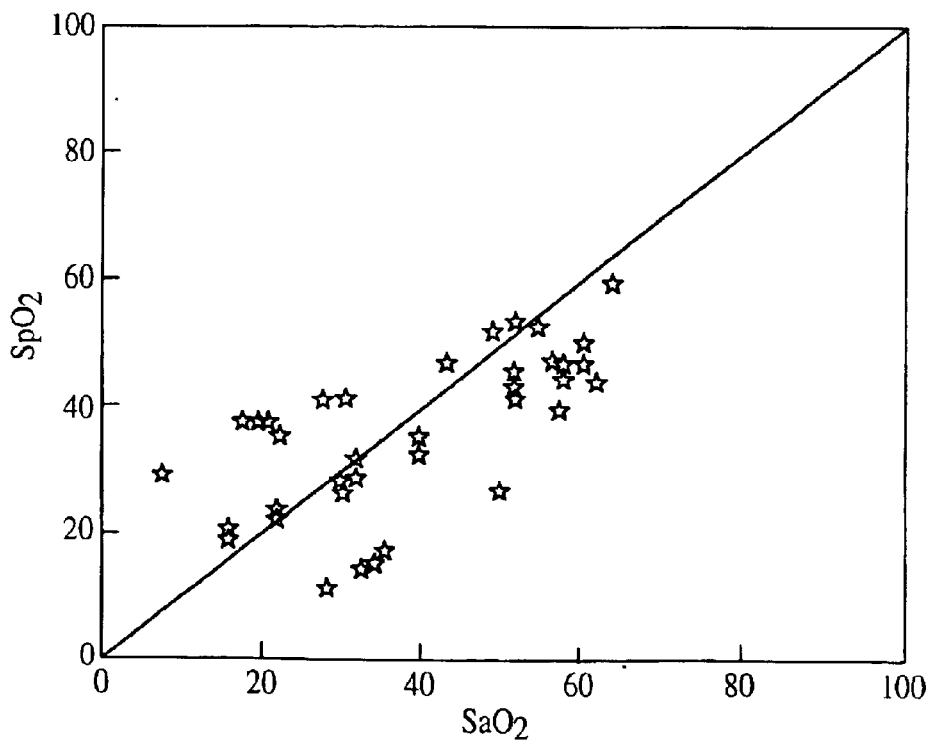
FIG. 5B shows the correlation between $SaO_2$, as measured by a blood gas analyzer, and $SpO_2$, as measured by an oximeter using the prior art practice of employing a fixed calibration curve.

Typically, the ratio R is used to predict $SpO_2$ as shown in FIG. 5A. An example of the correlation between predicted $SpO_2$ to measured $SaO_2$ using previous oximetry practices, i.e., without incorporating the effects of light scattering and absorption, is shown in FIG. 5B. The methods and techniques of the present invention increase the predictability of $SaO_2$, as shown in FIGS. 6B and 7B.

To evaluate the increased predictability of $SaO_2$ by incorporating $k_{DC}$ into the calibration process of $SpO_2$ measurement, a series of in vivo trials were conducted. The trials utilized time-dated pregnant ewes with singleton fetuses. The ewes were housed indoors in individual study cages and acclimated to controlled conditions of light (0600–1800 hrs.) and temperature (72° F.). Water and food were provided ad libitum, except for a 24-hour period prior to surgery. Under general anesthesia, the ewes were prepared with vascular catheters (femoral artery and vein) and a tracheal catheter. Fetuses were prepared with carotid artery and jugular vein catheters and two fetal scalp oximetry electrodes secured to the fetal head. An amniotic fluid catheter was also inserted. The study was performed in anesthetized ewes with fetuses maintained within the uterus.

The study consisted of a 1 hour basal period followed by a 3.5-hour hypoxia. During the basal period a maternal tracheal infusion of compressed air (5 L/min.) was administered continuously. Fetal and maternal heart rate and fetal oximetry were monitored continuously. Maternal arterial and fetal arterial and venous blood samples were drawn at 15 minute intervals for determination of pH, $pO_2$, $pCO_2$, $SO_2$, and $HCO_3$. At the end of the basal period, the maternal tracheal infusion was changed to a mixture of air and nitrogen gas with the rate being adjusted at 30 minute intervals to achieve a ramped 30 percentage point decrease, e.g., 50% to 20%, in fetal oximetry ($SpO_2$) in five (5) percentage point increments. The nitrogen mixture was titrated to maintain each $SO_2$ value for 30 minutes. After a ramped 30 percentage point decrease, fetal $SO_2$ was ramped back up to the basal value.

Fetal scalp oximetry ($SpO_2$) was correlated with arterial and venous $SO_2$. Using Equation (14), $k_{DC}$ is estimated, in one embodiment of the present invention, i.e., by ignoring the effects of background absorption and scattering, as follows:

$$k_{DC} \cong \frac{DC(\text{red})}{DC(ir)} \qquad \text{(Equation 17)}$$

Figure 6A:
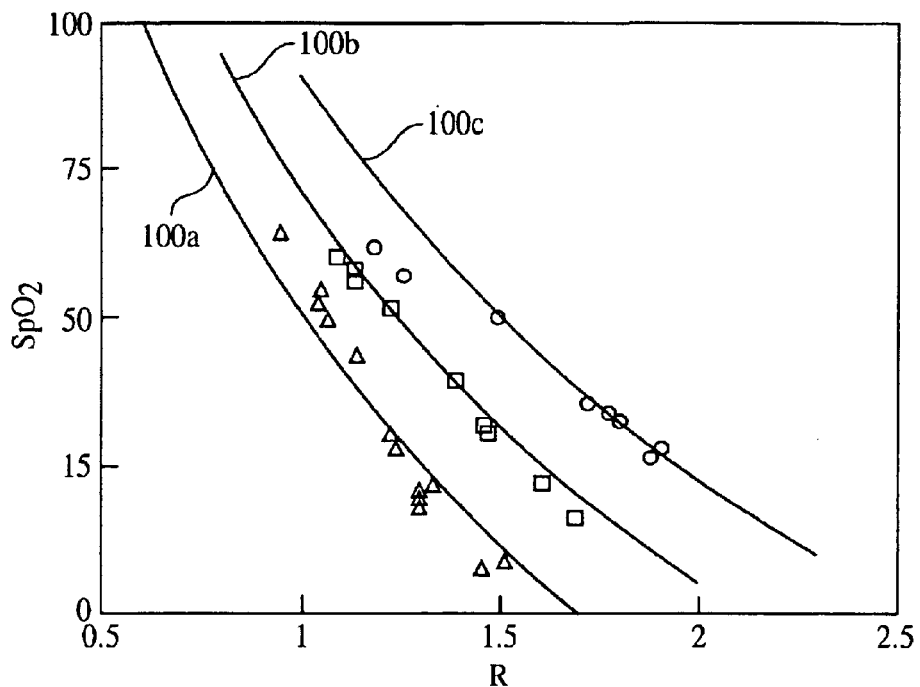
FIG. 6A shows the calibration curves for $SpO_2$ vs. R obtained by accounting for the scattering and absorption of light by employing Equation (17) for the same data from three clinical cases depicted in FIG. 5A.
Figure 6B:
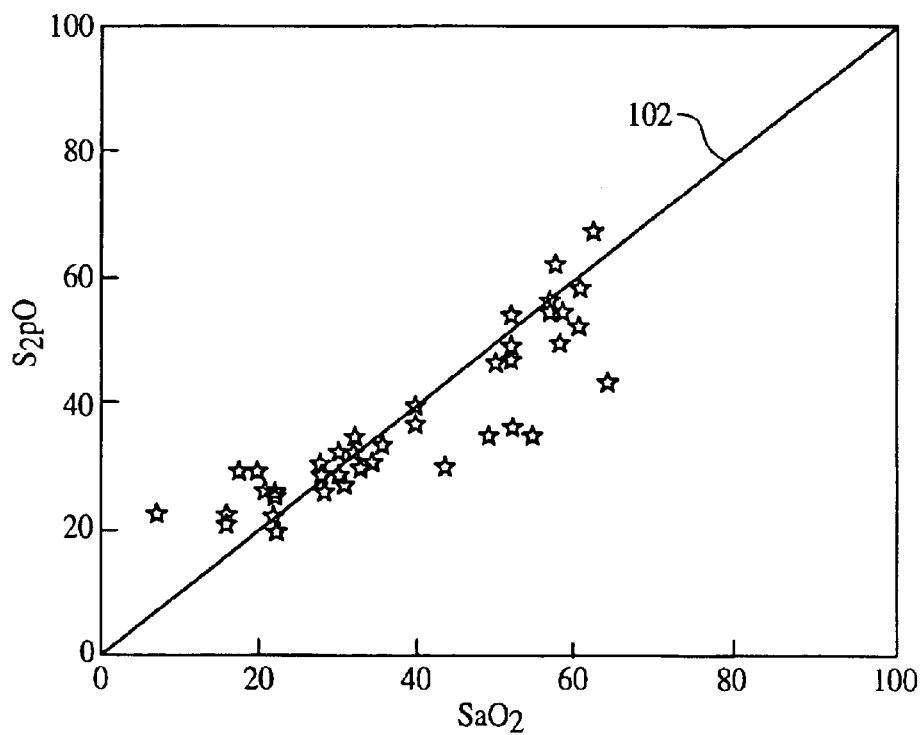
FIG. 6B shows the correlation between $SaO_2$, as measured by a blood gas analyzer, and $SpO_2$, as measured by an oximeter employing the dynamic calibration methodology of the present invention as represented by Equation (17)

FIG. 6A, illustrates calibration curves 100a, 100b, and 100c obtained using Equation (17) for three clinical cases using a Respironics Fetal Oximeter of the type described in U.S. application Ser. No. 09/581,122 on sheep fetuses. The contents of U.S. application Ser. No. 09/581,122 are incorporated herein by reference. FIG. 6B shows the correlation 102 between arterial hemoglobin oxygen saturation measured by the pulse oximeter ($SpO_2$) vs. the corresponding arterial saturation ($SaO_2$) measured using a blood gas analyzer.

The approximation shown in Equation (17) in the evaluation of $k_{DC}$ is based on the assumption that background absorption and scattering are ignored, such that:

$$D_r = \frac{\left.\frac{\partial T}{\partial \mu_a}\right|_{\mu_a=\mu_a(ir)}}{\left.\frac{\partial T}{\partial \mu_a}\right|_{\mu_a=\mu_a(red)}} \cong 1 \qquad \text{(Equation 18)}$$

Based on analysis of clinical data obtained from the experiments described above on sheep fetuses, it was determined, in actuality, that, $$0.75 < D_r < 1.30 \qquad \text{(Equation 19)}$$

and, thus, Equation (17) constitutes an acceptable approximation. It should be noted that FIG. 6B illustrates the same data as FIG. 5B, however, the $SpO_2$ vs. $SaO_2$ graph has been drawn based upon $k_{DC}$ being calculated with the estimation of Equation (17).

While there is no specific reason to choose a linear approximation, a simple estimation of $D_r$ is possible by assuming that it is linearly dependent on the ratio of the DC signals such that $$\xi = \frac{DC(\text{red})}{DC(ir)}.$$

By analyzing the clinical data obtained from the fetal sheep, the following was derived:

$$D_r = \begin{cases} -10\xi + 6.6, & \xi < 0.59 \\ -20\xi + 13.6, & 0.59 \leq \xi < 0.62 \\ -3.5\xi + 3.37, & 0.62 \leq \xi < 0.74 \\ -13.3\xi + 11.5, & 0.74 \leq \xi < 0.78 \\ -3.66\xi + 3.96, & \xi \geq 0.78 \end{cases} \qquad \text{(Equation 20)}$$

Where Equation (21) is used to calculate $k_{DC}$ as follows:

$$k_{DC} = D_r \frac{DC(\text{red})}{DC(ir)}. \qquad \text{(Equation 21)}$$

Alternate approximations that embody the $k_{DC}$ parameter can also be used in the practice of the present invention. For example, Equation (22) shows an alternative relationship between $k_{DC}$ and R:

$$k_{DC} = aR + b. \qquad \text{(Equation 22)}$$

In this equation, coefficients a and b are constants and have been determined from an analysis of the clinical data from the above described experiments to have optimal values of a=0.375, and b=0.225.

To practice the systems and methods of this invention by including $k_{DC}$, (in correlating $SaO_2$ to $SpO_2$) the scattering and absorption of light is accounted for, and the process and the prediction of $SaO_2$ is more precise. This holds true regardless of whether $k_{DC}$ is obtained by way of derivative evaluation, e.g., Equation (21), or through linear expression, e.g., Equation (22).

Figure 7A:
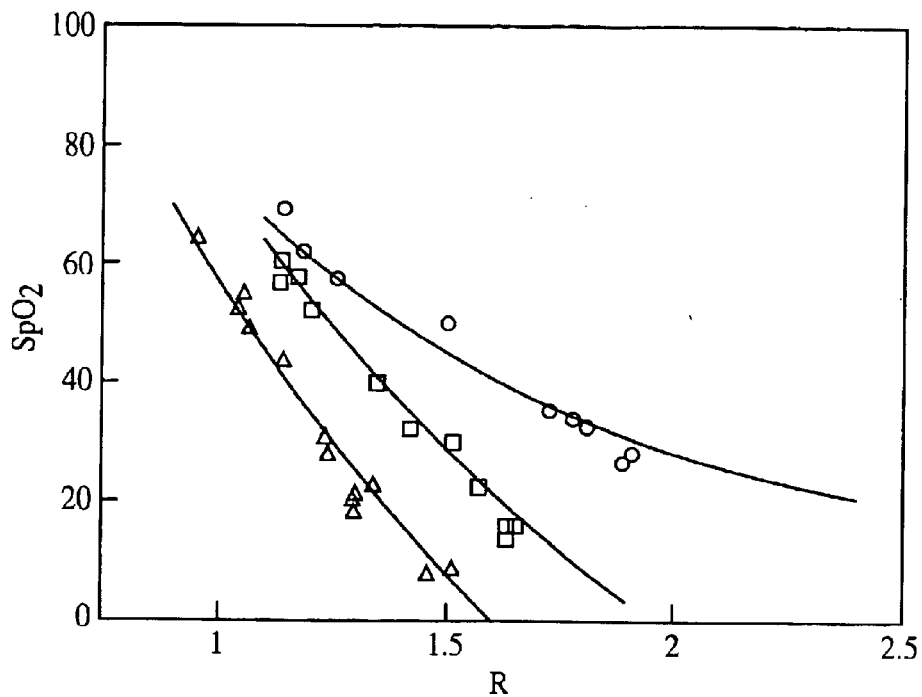
FIG. 7A shows the calibration curves for $SpO_2$ vs. R obtained by employing Equation (21) for the same data from three clinical cases depicted in FIGS. 5A and 6A.
Figure 7B:
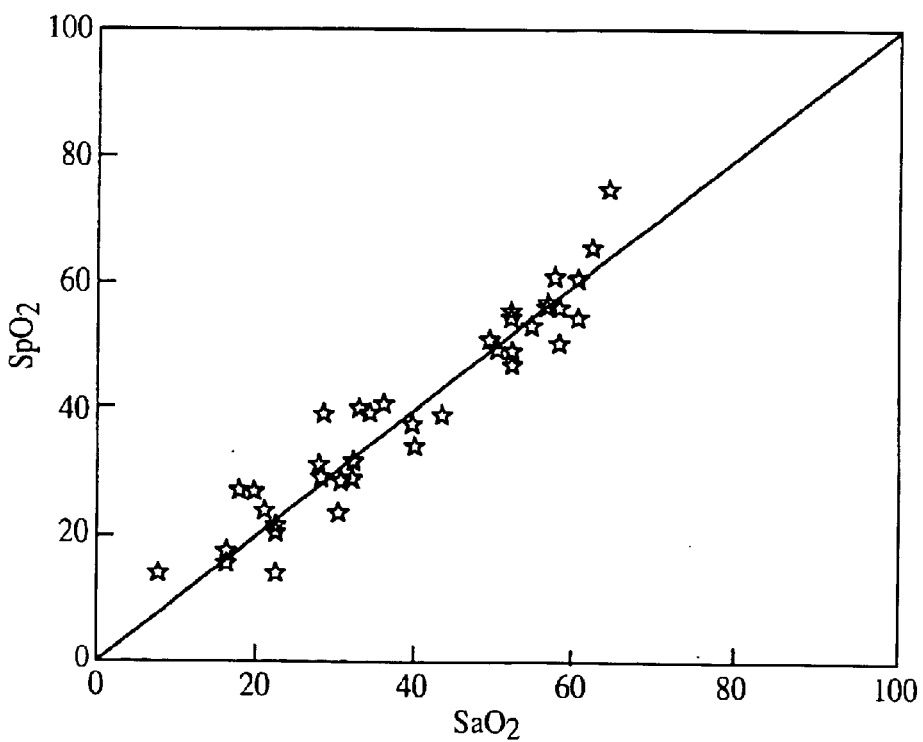
FIG. 7B shows the correlation between $SaO_2$, as measured by a blood gas analyzer, and $SpO_2$, as measured by an oximeter employing the dynamic calibration methodology of the present invention by incorporating the parameter $D_r$ as shown in Equation (21)

For example, FIG. 7A shows the calibration curves needed to predict $SaO_2$ as a function of the parameter R based upon the same data from the sheep clinical trials shown in FIG. 6A. The difference between the calibration curves of FIG. 7A and FIG. 6A is that in FIG. 7A, $SaO_2$ is calculated using the derivative values shown in above Equation (21).

FIG. 5B shows $SaO_2$ as measured by a blood gas analyzer, compared to $SpO_2$ as obtained by employing the traditional method of using a fixed calibration curve, i.e., the current practice in the calibration of pulse oximeters.

FIG. 6B shows $SaO_2$ vs. $SpO_2$ using estimation of $D_r = 1$ as detailed in Equation (18) above.

FIG. 7B incorporates the same data as in FIG. 5B, i.e., fixed calibration curve, and 6B, i.e., $D_r \cong 1$, but uses Equation (21) to further refine the correlation between $SaO_2$ by $SpO_2$.

Comparison of FIG. 5B with FIGS. 6B and 7B illustrates the improvements in the $SaO_2$ prediction achieved by employing the calibration techniques of the present invention.

While specific embodiments and methods for practicing this invention have been described in detail, those skilled in the art will recognize various manifestations and details that could be developed in light of the overall teachings herein. Accordingly, the particular arrangements disclosed are meant to be illustrative only and not to limit the scope of the invention which is to be given the full breadth of the following claims and any and all embodiments thereof.

What is claimed is:

1. A method of calibrating a pulse oximeter comprising:
   selecting a probe having an emitter, a detector, and a pathlength between the emitter and detector;
   measuring transmission of light through a tissue of interest with the probe;
   compiling a database of measured values characterizing the transmission of light through such a tissue;

formulating a value for a parameter $k_{DC}$ as a function of at least one of the measured values, wherein $k_{DC}$ is determined based only on empirical data; and incorporating the parameter $k_{DC}$ into a calibration equation for determining a value for $SpO_2$, wherein the calibration equation includes using $k_{DC}$ as a multiplier for a value determined from the measured values.

2. The method of claim 1, wherein the tissue of interest is a living being.

3. The method of claim 2, wherein the steps of measuring, compiling, formulating, and incorporating are repeated for the living being over a range of $SaO_2$ levels.

4. The method of claim 3, wherein the range of $SaO_2$ levels is greater than 70%.

5. The method of claim 3, wherein the range of $SaO_2$ levels is between about 15% and about 65%.

6. The method of claim 1, wherein the probe is an invasive probe.

7. The method of claim 1, wherein the probe's pathlength is approximately 1 mm to about 5 mm.

8. The method of claim 1, wherein, in the formulating step, the measured value includes a DC value.

9. The method of claim 1, wherein, in the compiling step, the measured values includes an AC and a DC component.

10. The method of claim 1, wherein, before the incorporating step, the measured values are used to calculate a Ratio R as the value for which $k_{DC}$ is used as the multiplier.

11. A method of performing optical blood oximetry comprising:

measuring the transmission of light through tissue;

determining at least one DC value based upon the transmission of light measurements;

selecting a calibration parameter $k_{DC}$ based upon the determined DC value, wherein the calibration parameter is determined based only on empirical data; and estimating $SaO_2$ based upon the selected calibration parameter by using the calibration parameter as a multiplier for a value determined from the measuring step.

12. The method of claim 11, further comprising the step of providing updated oxygen saturation estimates adapted to changes in the measured transmission.

13. The method of claim 11, further comprising providing a pulse oximeter probe that includes a light source capable of emitting light at two or more wavelengths, a detector, and a measurable distance between the light source and the detector.

14. The method of claim 11, wherein the step of determining further includes:

quantifying an AC value based upon the transmission of light;

calculating a Ratio R; and relating R to the calibration parameter that accounts for background absorption and scattering of light.

15. The method of claim 11, wherein the estimating step comprises:

quantifying the $k_{DC}$ value; and selecting a corresponding $SaO_2$ based upon previously determined clinical data.

16. A method of performing optical blood oximetry comprising:

measuring the transmission of light through tissue;

determining at least one DC value based upon the transmission of light measurements;

selecting a calibration parameter $k_{DC}$ based upon the determined DC value, wherein $k_{DC}$ includes a partial derivative $D_r$ value; and estimating $SaO_2$ based upon the selected calibration parameter.

17. A method of performing optical blood oximetry comprising:

(a) measuring the transmission of light through tissue;

(b) determining at least one DC value based upon the transmission of light measurements by performing the steps including:

(1) quantifying an AC value based upon the transmission of light, (2) calculating a Ratio R, and (3) relating R to the calibration parameter that accounts for background absorption and scattering of light including determining a partial derivative $D_r$ value, and using the $D_r$ value to relate R to the calibration parameter;

(c) selecting a calibration parameter $k_{DC}$ based upon the determined DC value; and (d) estimating $SaO_2$ based upon the selected calibration parameter.

18. A method of performing optical blood oximetry comprising:

(a) measuring the transmission of light through tissue;

(b) determining at least one DC value based upon the transmission of light measurements by performing the steps including:

(1) quantifying an AC value based upon the transmission of light, including estimating a partial derivative $D_r$ value, (2) calculating a Ratio R, and (3) relating R to the calibration parameter that accounts for background absorption and scattering of light;

(c) selecting a calibration parameter based upon the determined DC value; and (d) estimating $SaO_2$ based upon the selected calibration parameter.

19. A physiological condition measuring device comprising:

light generating means;

light detecting means, wherein an optical path having pathlength is defined between the light generating means and the light detecting means; and a processing system that measures light incident upon the light detecting means and returns a solution determined from a calculation that includes multiplying (1) a value determined from the measured light and (2) a calibration parameter $k_{DC}$ that is based only on empirical data.

20. A measuring device according to claim 19, wherein the physiological condition is oxygen saturation.

21. The apparatus of claim 20, further comprising means for adaptively calibrating the predicted arterial oxygen saturation in response to the signals received from the probe.

22. A measuring device of claim 19, wherein the processing system produces a measurement of $SpO_2$.

23. A measuring device according to claim 19, wherein the optical pathlength is less than about 1 cm.

24. A measuring device according to claim 19, wherein the processing system is calibrated to measure $SaO_2$ in a range of about 10% to about 70%.

25. An apparatus for determining oxygen saturation of hemoglobin in arterial blood using signals received from a probe, the signals being indicative of the light absorption of arterial blood, which has pulsatile and non-pulsatile components, at two or more light wavelengths, the apparatus comprising:

means responsive to the signals received from the probe;

means for convening the signals received into data;

memory means for storing the data;

computing means for calculating parameters from the data; and means for relating the calculated parameters to a predicted arterial oxygen saturation, that includes (1) selecting a calibration parameter $k_{DC}$ based upon the non-pulsatile components, wherein the calibration parameter is determined based only on empirical data, and (2) estimating oxygen saturation based upon (a) the selected calibration parameter and (b) the calculated parameters, wherein estimating the oxygen saturation includes using the calibration parameter as a multiplier for the calculated parameters.

26. A system for performing pulse oximetry comprising:

a probe including at least one light source for transmitting light and at least one detector for detecting the transmitted light;

a processing system in communication with the probe so as to receive signals from the probe, wherein the processing system (a) determines data corresponding to 1) first variables indicative of the optical parameters of a tissue being probed based on the received signals and 2) second variables related to a parameter $k_{DC}$ that is determined based only on empirical data and that accounts for the scattering and absorption of light by the tissue, and (b) determines an estimate of oxygen saturation by performing a calculation that includes multiplying the first variables by the second variables.

* * * * *